US00PP20109P3

(12) United States Plant Patent
Worthington

(10) Patent No.: US PP20,109 P3
(45) Date of Patent: Jun. 23, 2009

(54) SHANTUNG MAPLE TREE NAMED 'WF-AT1'

(50) Latin Name: *Acer truncatum*
Varietal Denomination: WF-AT1

(75) Inventor: Michael W. Worthington, Greenville, NC (US)

(73) Assignee: Worthington Farms, Inc., Greenville, NC (US)

( * ) Notice: Subject to any disclaimer, the term of this patent is extended or adjusted under 35 U.S.C. 154(b) by 25 days.

(21) Appl. No.: 11/906,674

(22) Filed: Oct. 2, 2007

(65) Prior Publication Data

US 2008/0141408 P1 Jun. 12, 2008

Related U.S. Application Data

(60) Provisional application No. 60/851,796, filed on Oct. 12, 2006.

(51) Int. Cl.
*A01H 5/00* (2006.01)

(52) U.S. Cl. ..... Plt./224

(58) Field of Classification Search ..... Plt./224
See application file for complete search history.

*Primary Examiner*—S. B. McCormick Ewoldt

(57) ABSTRACT

'WF-AT1' is a new and distinct cultivar of *Acer truncatum* that is noted for its consistent orange-red autumn leaf color; its exceptional landscape stress tolerance; and its compact, round-canopied form with ascending branches.

3 Drawing Sheets

Latin name of the genus and species of the plant claimed: *Acer truncatum.*

Variety denomination: 'WF-AT1'.

BACKGROUND OF THE INVENTION

The Latin names and authority of the new cultivar described and disclosed herein is *Acer truncatum* Bunge, commonly known as Shantung maple, Shundong maple, or purple-blow maple.

The genus *Acer* comprises a diverse group of temperate-zone deciduous and evergreen trees and/or shrubs, commonly called "maple(s)." *Acer truncatum*, introduced into cultivation in 1881, is only now being considered more widely as an ornamental, deciduous landscape tree, and small-sized street tree. *Acer truncatum* is native to northern and northeastern China, and also far eastern Russia, the Korean peninsula, and Sakhalin Island.

*Acer truncatum* is classified within *Acer* Section *Platanoidea,* a subgeneric grouping of closely related maples that includes 10 species. Within this section are other familiar species, including *Acer platanoides* (commonly known as Norway maple) and *Acer campestre* (commonly known as hedge maple). However, *Acer truncatum* is not closely related to *Acer saccharum* (commonly called sugar maple), despite the superficial resemblance of the leaves of these 2 species. Unlike *Acer saccharum, Acer truncatum* is most readily distinguished by its white, latex-bearing sap (a trait of all species of *Acer* Section *Platanoidea*) and its spring growth flush that is variously colored in bronze to orange to reddish tones. Under cultivated conditions, *Acer truncatum* matures as a small-sized tree reaching up to 25 to 33 feet (7.5 to 10 m) tall and bearing a round-headed canopy. All three of these other maples, *Acer platanoides, A. campestre,* and *A. saccharum,* mature at substantially larger sizes than does *A. truncatum.* Only with great age can *Acer truncatum* reach heights comparable to those of medium- to large-sized trees, as specimens of 55 to 70 feet (16.5 to 21 m) are known in cultivation, and heights of 75 feet (23 m) have been reported from the wild. In cultivation in the U.S., *Acer truncatum* is highly regarded for its lack of susceptibility to any major pests, diseases, and insects. *Acer truncatum* is a widely adapted species that is cold hardy to USDA Zone 4 and also prospers in the heat of USDA Zone 9.

My new 'WF-AT1' variety originated in 1998 from sown seed that gave rise to a seedling plant growing in a field nursery block 5 miles west of Greenville, N.C. (Pitt County). The origin of the seed was from a commercial nursery, of true-to-type source, and was not from a pre-existing cultivar of *Acer truncatum.* Therefore, the seed source from which 'WF-AT1" is derived is based on an unpatented, undisclosed mother plant of *Acer truncatum.* Occurring in a seed-block, along with other trees of *Acer truncatum,* one tree stood out for its vigor, attractive foliage qualities throughout the growing season, and especially its flaming orange-red fall color. This tree was subsequently marked and held for further observation. Since 1998, this original tree of the 'WF-AT1' variety has grown to 19 feet (5.8 m) tall by 13.5 feet (4.1 m) wide and has a trunk diameter (dbh) of 6.75" (17 cm), as of December, 2005. The 'WF-AT1' has been asexually propagated at my direction in Pitt County, N.C., via budding and grafting. This propagation and observations of the resulting progeny have proven the characteristics of my new variety to be firmly fixed and reproduce true to type. Furthermore, these observations have confirmed that my new variety represents a new and improved variety of Shantung maple tree.

BRIEF SUMMARY OF THE INVENTION

'WF-AT1' is characterized to novelty as an *Acer truncatum* tree with relatively small leaves and a consistent display of orange-red autumn leaf color, even in warm temperate climates. 'WF-AT1' is not susceptible to insect pests and diseases and is considered to be hardy in USDA Zones 4 through 9. 'WF-AT1' is being tested and growing in USDA Zones 6 to 9.

BRIEF DESCRIPTION OF THE DRAWINGS

Colors as shown in these drawings were taken under conditions of natural lighting in an outdoor setting. However, although the colors are believed to be as true as possible, digital capture and subsequent reproduction of these drawings may not accurately represent the true color. As such, chromal characteristics of this new plant should be taken as described below in the botanical description, with the values cited based on the R.H.S. Colour Chart, 2001 edition.

DETAILED BOTANICAL DESCRIPTION

Figure 1:
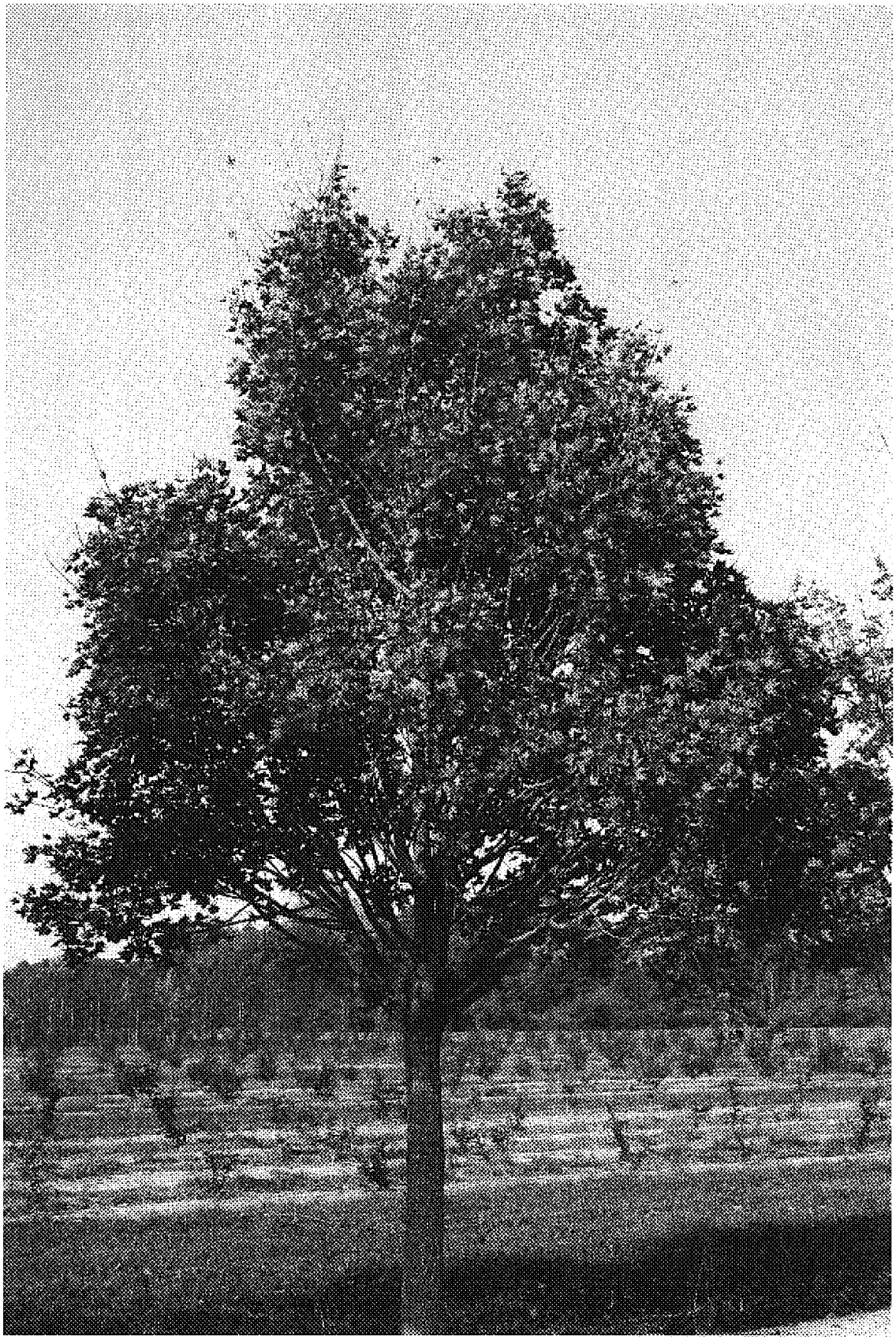
FIG. 1 illustrates the original 'WF-AT1' maple tree growing in Pitt County, N.C. at peak fall color. The form of the tree is also evident from this illustration.
Figure 2:
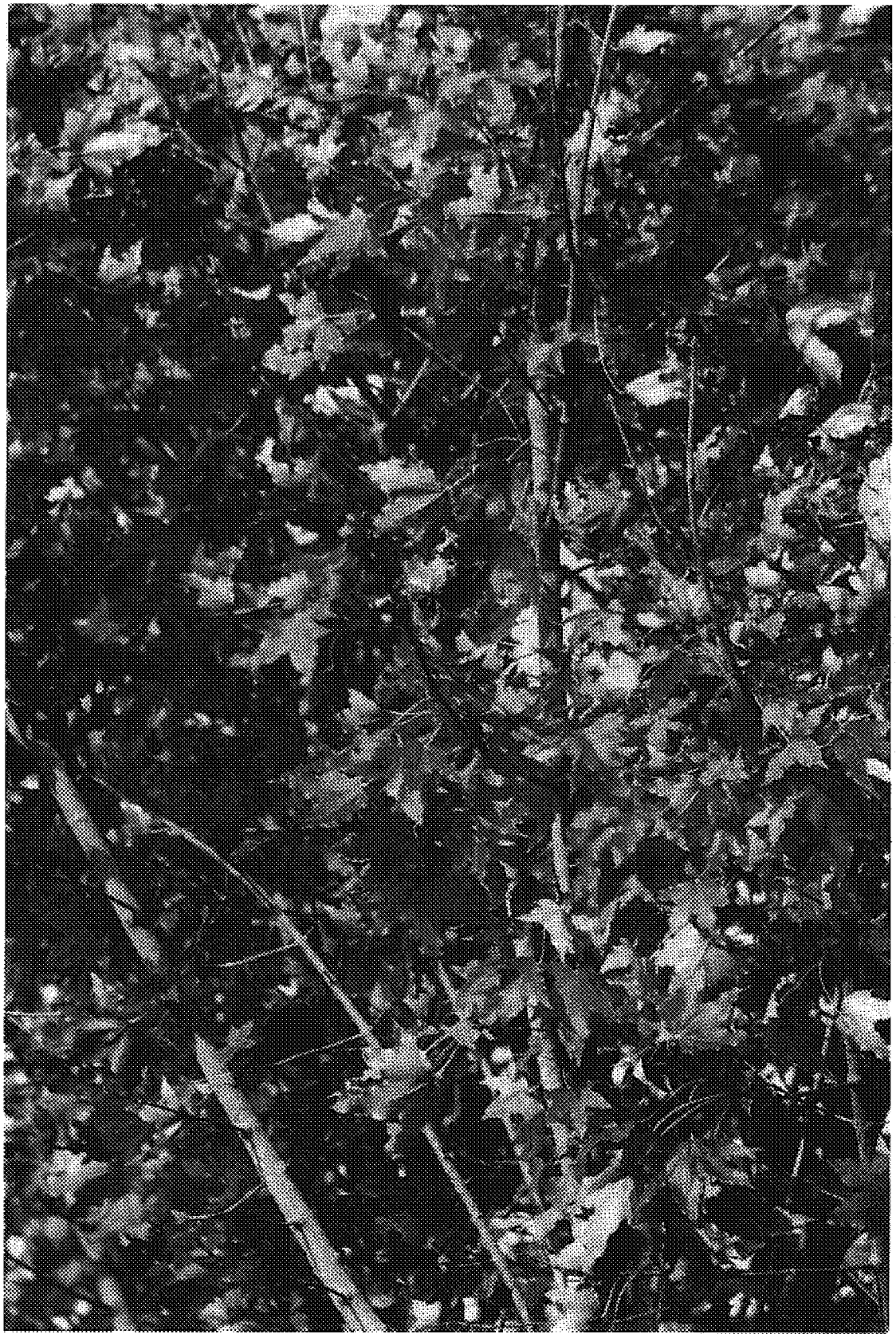
FIG. 2 illustrates foliage and branches of the original 'WF-AT1' maple tree growing in Pitt County, N.C. at peak fall color.
Figure 3:
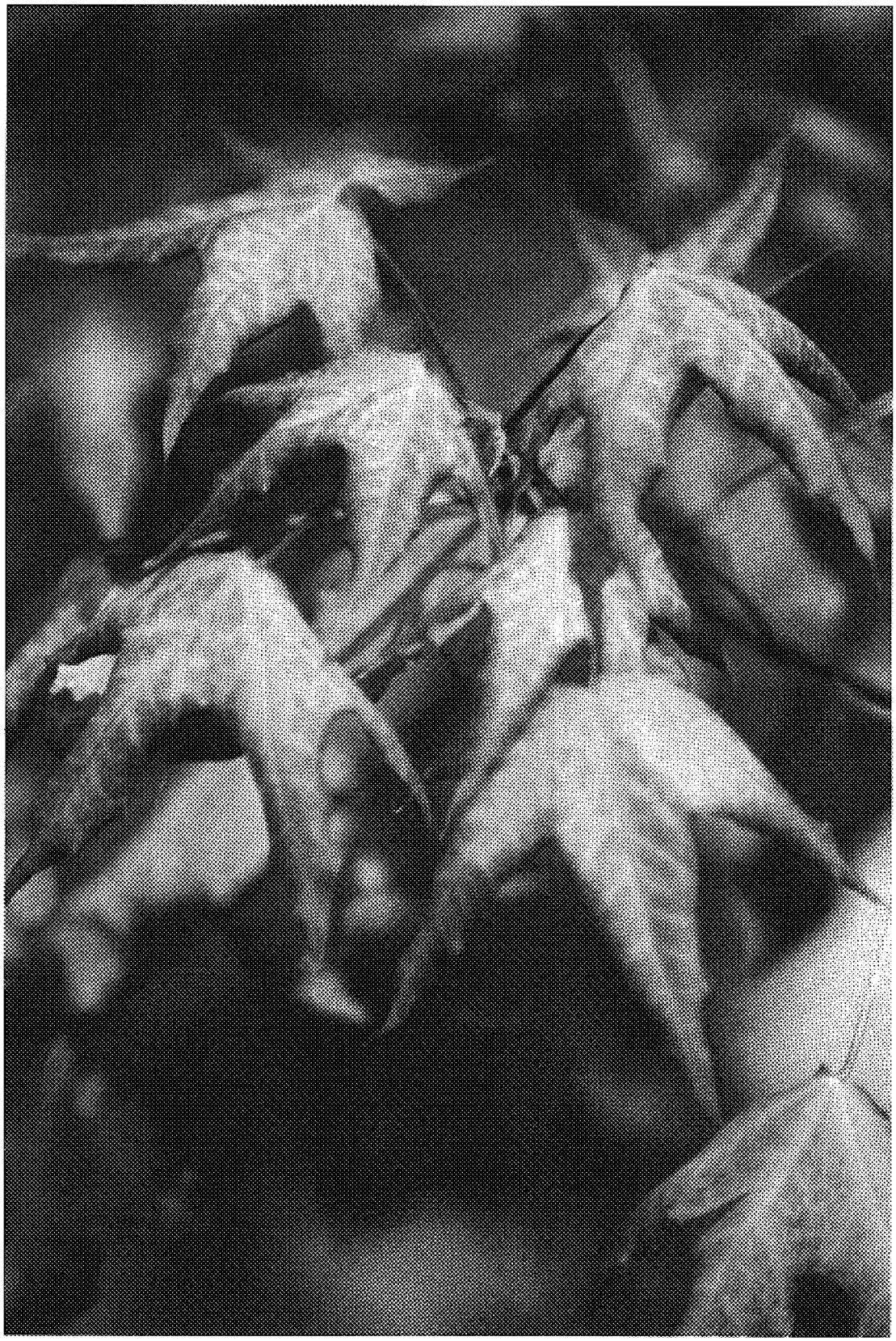
FIG. 3 illustrates a close-up view of emerging spring foliage of the original 'WF-AT1' maple tree growing in Pitt County, N.C. Note the different colors of the foliage from the margins of the leaf lobes to the center portion of these lobes.

The following detailed botanical description pertains to *Acer truncatum*,'WF-AT1' based on data collected from the now 8 year-old, original 'WF-AT1' tree (the founder tree) growing in Pitt County, N.C. All data presented are based on multiple samples, of which means are presented and number of samples averaged is indicated by "N=x" where "N" refers to the statistical sample size and "x" refers to the actual number of samples from which data were collected.

Beginning in spring 2005, data were collected on the founder tree of 'WF-AT1' to assess biometric data and color values. These data were collected again in late summer, and again in fall at time of peak autumn foliar coloration. All color notation data is based on The Royal Horticultural Society Colour Chart, The Royal Horticultural Society, London, 2001, except in cases when general descriptive color terminology is used for the sake of simplicity and brevity.

*Acer truncatum* is considered to be a small-sized deciduous tree, with height remaining at or below 33 feet tall (10 m) after 10 years of growth, to which 'WF-AT1' conforms. Growth form is strictly deliquescent, with no obvious excurrent growth form even in youth. This deliquescent growth form is evidenced by the compact, round-headed canopy that forms on trees, even when young and without any strict pruning regime. Branch angles of 'WF-AT1' are narrow (usually 45° or higher), with secondary branches ascending; but not so narrow as to lead to problems of bark inclusions or weak trunk/branch unions.

Bark of *Acer truncatum* and of the 'WF-AT1' variety is somewhat lustrous, brown to brown-purple in color, and glabrous on younger twigs and branches, becoming greyed brown on older branches, and moderately lenticellate. Bark texture on these twigs to small branches is rough to somewhat corky. Older trees of both the 'WF-AT1' variety and of *Acer truncatum* exhibit a diagnostic and readily distinguishable rough, deeply fissured bark. Bark of emerging twigs (early spring) of 'WF-AT1' are colored red-purple (between RHS 59A to 60A). Midseason (e.g., late summer) twig bark color on 'WF-AT1' is greyed-orange (RHS 177C) on youngest twig portions, and greyed-orange (RHS 177D) on older twig portions. Bark on large branches and the trunk is smooth and greyed green (between RHS 195A and 196A) in color. Fissures in the bark are somewhat shallow (<0.5 cm) in depth, and bark tissue within these fissures is greyed-orange (RHS N167A) in color. These bark attributes of the trunk and larger branches are consistent for *Acer truncatum* and for the 'WF-AT1' variety.

Dormant buds on 'WF-AT1' (terminal buds only) are nearly 0.25 inches (0.6 cm) tall, 4-sided, and glabrous except on the apices of the bud scales. Bud scales of 'WF-AT1' are colored greyed-orange (RHS 177D) in 'WF-AT1', and are arranged imbricately. Lateral buds are greatly reduced in size in comparison to terminal buds. Phyllotaxy is opposite and decussate in 'WF-AT1', as is the case for *Acer.* Leaves of the 'WF-AT1' variety are borne on long, slender petioles. Petiole color of the 'WF-AT1' variety changes with the season, as does that of the leaf.

Leaves of *Acer truncatum* are lobed, with 5 lobes being more prevalent, but some trees bearing 7 lobes. In 'WF-AT1' leaves consistently bear 5 lobes. Leaves of 'WF-AT1' are glabrous above, with only axillary tufts of pubescence found on the leaf undersides at the point where the primary veins and midrib meet the petiole at the leaf base. 'WF-AT1' leaf lobes are broad at their bases, tapering to acuminate apices. Leaves of *Acer truncatum* and 'WF-AT1' are thin-textured, measuring less than 1 mm in thickness.

*Acer truncatum* can be notable for the color of its new growth flush in spring, ranging from yellow-green to red-purple to red. In 'WF-AT1', leaves emerge in spring colored red-purple (between RHS 59A and 59B), and upon fully expanding become yellow-green (RHS 144B and 144C). Color progression within 'WF-AT1' leaves is such that yellow-green pigments are seen both at the leaf bases and radiating outward from the veins; while red-purple color is retained at lobe apices, interveinal areas of the lobes, and leaf margin. Primary leaf veins are colored RHS N144A as the new growth flush is occurring. Twig color is red-purple (RHS 59A to 60A) on the emerging 'WF-AT1' spring growth flush, matching that of the leaves. Petioles in young, newly emerging 'WF-AT1' leaves are red-purple (RHS 60A). Leaf color in mid- to late-summer of 'WF-AT1' is yellow-green, with the upper leaf lamina colored an attractive dark yellow-green (RHS 147A) and the petiole colored a much brighter yellow-green (RHS 150B). Leaf venation is palmate, and the primary veins of each lobe are colored yellow-green (RHS 147C) in mid- to late-summer.

In autumn, 'WF-AT1' is readily distinguished by its brightly colored leaves. Leaf lamina, petiole, and primary veins are colored orange (RHS 25A or N25A or N25B), orange-red (RHS 34A or 34B or N34A) or red (RHS 46B). These fall colors persist for over two weeks. Leaves throughout the entire canopy are vibrantly colored. This fall color behavior has been repeated through over 8 years of observations of the founder tree of 'WF-AT1' and has been reproduced in all plants propagated from the founder tree growing in Greenville, N.C.

In the absence of the diagnostic autumn foliage coloration, 'WF-AT1' will be identifiable by the dimensions of its leaves. In *Acer truncatum,* leaf shape, leaf size, lobe number, and lobe size can vary considerably; whereas at the clonal level, such as in 'WF-AT1', no such variation should be seen across a field or container production block in a nursery setting. Leaves of the founder tree of 'WF-AT1' were collected and measured at 2 points during the growing season in Pitt County, N.C.: early spring (April) and late summer (September). A random sampling of leaves to be measured was collected from subterminal positions (usually 3–4 nodes back from the terminal bud or terminal leaf pair) along the current season's twigs. Only leaves that were directly exposed to sunlight were collected. Lobe number is arranged from left to right for the 5 lobes, as viewed when the adaxial leaf surface is facing upward. Likewise, sinus number refers to the sinuses as viewed from left to right when the leaf is similarly oriented. Table 1 summarizes this biometric data collected on the foliage of *Acer truncatum 'WF-AT*1'.

Just prior to full expansion of the new shoot (leaves and stem) in spring, 'WF-AT1' bud scales swell and break open. At this point, bud scales are 0.16 to 0.47 inches (4 to 12 mm) long by 0.04 to 0.08 inches (1 to 2 mm) wide. These bud scales are moderately caducous, persisting for 4 to 10 days after the occurrence of budbreak. The terminal-most 2 bud scales develop into a vestigial, leaf-like structure, with a defined, channeled (canaliculate) stalk and a 3-lobed apex, wherein the 3 lobes of these terminal-most bud scales resemble tiny, bract-like leaves or bract-like lobes of a lobed leaf. These modified bud scale-like to vestigial leaf-like structures are brightly colored in 'WF-AT1'. The stalk of this structure is red (RHS 46A); while the 3-lobed apical bract-like structure is yellow (RHS 10B, or 10A).

*Acer truncatum* is an andromonoecious species, meaning that both male and complete (bisexual) flowers are produced on the same plant. 'WF-AT1' conforms to this trait; although flowers have been observed only sporadically thus far only on the parent tree. Neither fruit nor seed have yet been observed on 'WF-AT1'. As with the species, flowers of 'WF-AT1' are borne in erect, terminal corymbs, with inflorescences measuring 2.4 to 3.2 inches (6 to 8 cm) across and supported by peduncles 0.4 to 0.8 inches (1 to 2 cm) in length. Individual flowers bear 5 yellow-green (RHS 1B) sepals 0.16 to 0.20 inches (4 to 5 mm) in length and 5 yellow-green (1C) petals 0.20 to 0.28 inches (5 to 7 mm) in length. When in flower, trees of *Acer truncatum* are colored distinctly yellow-green in early spring due both to the great number of inflorescences and to their terminal positions atop the new growth.

Comparisons With Other Related Taxa

The 'WF-AT1' variety is readily distinguished from *Acer truncatum* 'Akikaze Nishiki' by its absence of variegation. The 'WF-AT1' variety is also readily distinguished from both 'Warrenred' (PP7,433) and 'Keithsform' (PP7,529) by its finer texture and smaller leaves, as shown in Table 2.

TABLE 1

Leaf dimensions [inches (cm)] of *Acer truncatum* 'WF-AT1'[1].

| | early spring (April) | late summer (September) |
|---|---|---|
| number of lobes | 5 | 5 |
| petiole length | 3.2 (8.2) | 3.7 (9.3) |
| leaf width[2] | 4.0 (10.1) | 4.1 (10.5) |
| leaf length[3] | 2.6 (6.6) | 3.0 (7.6) |
| lobe #1 length[4] | 2.0 (5.2) | 2.1 (5.4) |
| lobe #2 length[4] | 2.5 (6.3) | 2.7 (7.0) |

TABLE 1-continued

Leaf dimensions [inches (cm)] of *Acer truncatum* 'WF-AT1'[1].

| | early spring (April) | late summer (September) |
|---|---|---|
| lobe #4 length[4] | 2.4 (6.1) | 2.8 (7.1) |
| lobe #5 length[4] | 2.0 (5.2) | 2.1 (5.4) |
| lobe #1 width[5] | 0.6 (1.6) | 0.8 (2.0) |
| lobe #2 width[5] | 0.9 (2.3) | 1.1 (2.8) |
| lobe #3 width[5] | 0.9 (2.3) | 1.2 (3.1) |
| lobe #4 width[5] | 0.9 (2.3) | 1.1 (2.8) |
| lobe #5 width[5] | 0.6 (1.6) | 0.8 (2.0) |
| sinus #1 depth[6] | 0.5 (1.2) | 0.6 (1.4) |
| sinus #2 depth[6] | 0.6 (1.6) | 0.7 (1.8) |
| sinus #3 depth[6] | 0.6 (1.6) | 0.7 (1.9) |
| sinus #4 depth[7] | 0.5 (1.2) | 0.6 (1.4) |
| sinus #1 width[7] | 1.8 (4.5) | 1.9 (4.9) |
| sinus #2 width[7] | 2.1 (5.3) | 2.6 (6.6) |
| sinus #3 width[7] | 2.0 (5.1) | 2.7 (6.8) |
| sinus #4 width[7] | 1.6 (4.1) | 2.0 (5.1) |

[1]N = 10 for all characters quantified.
[2]Leaf width measured as distance from apex of left-most lobe (lobe #1) to apex of right-most lobe (lobe #5).
[3]Leaf length measured as distance from apex of center leaf lobe (lobe #3) to point of attachment of lamina to petiole. Leaf length refers to length of lamina only. Petiole length was quantified separately.
[4]Lobe length measured as distance for apex of lobe to point where lobe mid-rib vein meets leaf midrib (the latter equivalent to the midrib of lobe #3).
[5]Lobe width measured as distance across lobe at its base (= widest point).
[6]Sinus depth measured as average of margins of 2 adjacent lobes.
[7]Sinus width measured as distance from apex of left-adjacent lobe to apex of right-adjacent lobe.

TABLE 2

Comparison of *Acer truncatum* 'WF-AT1' with *Acer* 'Warrenred' (PP7,433) and *Acer* 'Keithsform' (PP7,529). [inches (cm)]

| | 'WF-AT1' | 'Warrenred' | 'Keithsform' |
|---|---|---|---|
| Leaf width[1] | 4.1 (10.5) | 5.5 (14) | 5.2 (13.3) |
| Leaf length[2] | 6.7 (17.0) | 7.2 (18.2) | 7.1 (18.1) |

[1]Leaf width of 'WF-AT1' measured as distance from apex of left-most lobe (lobe #1) to apex of right-most lobe (lobe #5). Leaf width of 'Warrenred' and 'Keithsform' data taken as reported in PP7,433 and PP7,529, respectively.
[2]Leaf length of 'WF-AT1' measured as distance from apex of center leaf lobe (lobe #3) to base of petiole. Leaf length of 'Warrenred' and 'Keithsform' data taken as reported in PP7,433 and PP7,529, respectively.

I claim:

1. A new and distinct tree of *Acer truncatum* named 'WF-AT1' substantially as herein shown and described, characterized particularly as to novelty by its consistent display of orange-red autumn leaf color, even in warm temperate climates.

* * * * *

UNITED STATES PATENT AND TRADEMARK OFFICE

CERTIFICATE OF CORRECTION

PATENT NO. : PP 20,109 P3
APPLICATION NO. : 11/906674
DATED : June 23, 2009
INVENTOR(S) : Michael W. Worthington It is certified that error appears in the above-identified patent and that said Letters Patent is hereby corrected as shown below:

Column 1, line 1, the following text should be added:

--CROSS REFERENCE TO RELATED APPLICATIONS
This application claims the benefit of US Provisional Application No. 60/851,796 filed October 12, 2006, herein incorporated by reference.

STATEMENT REGARDING FEDERALLY SPONSORED RESEARCH OR DEVELOPMENT
None.--

Signed and Sealed this

Second Day of February, 2010

David J. Kappos

David J. Kappos
*Director of the United States Patent and Trademark Office*